US004001575B2

United States Statutory Invention Registration [19]

[11] Reg. Number: H1575

Daugherty et al.

[45] Published: Aug. 6, 1996

[54] APERTURED HYDROPHILIC POLYMER FILM TOPSHEET WITH IMPROVED ABSORBENCY AND COMFORT PROPERTIES

[76] Inventors: Thomas H. Daugherty; Barbara J. H. Daugherty, both of The Procter & Gamble Company, Winton Hill Technical Center, 6100 Center Hill Rd., Cincinnati, Ohio 45224

[21] Appl. No.: 308,776

[22] Filed: Sep. 19, 1994

[51] Int. Cl.[6] ..... B32B 3/00

[52] U.S. Cl. ..... 428/284; 428/131; 428/132; 428/137; 428/286; 428/304.4; 428/308.4; 428/332; 428/409; 604/358; 604/366; 604/367; 604/370; 604/371; 604/372; 604/378; 604/385.1

[58] Field of Search ..... 428/131, 132, 428/137, 284, 286, 304.4, 308.4, 332, 409; 604/385.1, 378, 358, 366, 367, 370, 371, 372

[56] References Cited

U.S. PATENT DOCUMENTS

| | | | |
|---|---|---|---|
| 3,695,269 | 10/1972 | Malaney . | |
| 3,929,135 | 12/1975 | Thompson . | |
| 4,077,410 | 3/1978 | Butterworth et al. | 128/287 |
| 4,342,314 | 8/1982 | Radel et al. . | |
| 4,463,045 | 7/1984 | Ahr et al. . | |
| 4,480,000 | 10/1984 | Watanabe et al. . | |
| 4,540,414 | 9/1985 | Wishman . | |
| 4,578,066 | 3/1986 | O'Connor . | |
| 4,636,209 | 1/1987 | Lassen . | |
| 4,704,112 | 11/1987 | Suzuki et al. . | |
| 4,710,186 | 12/1987 | DeRossett et al. . | |
| 4,723,953 | 2/1988 | Rosenbaum et al. . | |
| 4,723,954 | 2/1988 | Pieniak . | |
| 4,728,694 | 3/1988 | Batich et al. . | |
| 4,734,445 | 3/1988 | Noda et al. . | |
| 4,735,843 | 4/1988 | Noda . | |
| 4,846,813 | 7/1989 | Raley . | |
| 4,908,026 | 3/1990 | Sukiennik et al. . | |
| 5,047,023 | 9/1991 | Berg . | |
| 5,074,854 | 12/1991 | Davis . | |
| 5,149,335 | 9/1992 | Kellenberger et al. . | |
| 5,176,672 | 1/1993 | Bruemmer et al. . | |
| 5,219,341 | 6/1993 | Serbiak et al. . | |
| 5,221,726 | 6/1993 | Dabi et al. . | |
| 5,234,422 | 8/1993 | Sneller et al. . | |
| 5,236,430 | 8/1993 | Bridges . | |
| 5,246,433 | 9/1993 | Hasse et al. . | |
| 5,360,421 | 11/1994 | Revelle . | |

FOREIGN PATENT DOCUMENTS

| | | |
|---|---|---|
| 245074 | 11/1987 | European Pat. Off. . |

*Primary Examiner*—Donald P. Walsh
*Assistant Examiner*—Chrisman D. Carroll

[57] ABSTRACT

An improved topsheet for use in absorbent articles such as sanitary pads. The topsheet comprises a three-dimensional hydrophilic formed film having a plurality of openings leading from a surface of the topsheet to an absorbent core. The topsheet presents a more comfortable and dryer surface which contacts the wearer and a clean, dry appearance to the wearer. The clean, dry appearance is obtained by employing an opacifying agent in the film. The openings comprise tapered capillaries having a base in the surface plane of the topsheet and an apex remote from the surface plane of the topsheet. Each apex is in intimate contact with the absorbent core. In a preferred arrangement, the hydrophilic polymer film topsheet comprises Nylon 6, Nylon 6 and polyetheramide, or other resins having chemistries similar to nylon.

20 Claims, 2 Drawing Sheets

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

APERTURED HYDROPHILIC POLYMER FILM TOPSHEET WITH IMPROVED ABSORBENCY AND COMFORT PROPERTIES

TECHNICAL FIELD

This invention relates to topsheets for absorbent devices such as diapers, sanitary pads, bed pads, incontinence pads, towels, bandages and the like, and, more particularly, to an improved absorptive topsheet structure which helps facilitate absorption and allows fluid to pass freely into the interior of an absorptive device, but which inhibits the reverse or outward flow of fluid. A topsheet is often the portion of an absorptive device which covers one face of the absorbent core and contacts the skin of the person using the absorptive device. The topsheet may have inverted, tapered capillary structures which provide an hydrophilic layer which enhances dependable absorption, comfort, and dryness performance characteristics of any of a variety of absorption devices.

BACKGROUND ART

Absorptive devices often comprise articles of manufacture designed to receive and retain bodily fluid discharges, with diapers, sanitary pads, bed pads, incontinence pads, towels, bandages and the like being well known. Disposable absorbent devices are designed to be used once and discarded, enhancing both convenience and hygiene.

Generally, known disposable absorptive devices comprise an absorbent core covered on one side with a topsheet which preferably contacts the body, and covered on the distal side with a fluid-impermeable backsheet. The backsheet prevents absorbed (bodily) fluids from leaking out of the device and soiling the wearer, clothing or bedding. Polymer film apertured topsheets, known in the art, are generally made of hydrophobic material (e.g., polyethylene) which is impervious or impermeable to liquids. A primary reason that fluid often remains in contact with the wearer's body is that hydrophobic polymer films, by their very nature, do not absorb moisture. Another disadvantage of conventional devices is discomfort due to the hot, sweaty, and sticky feel on the wearer's skin often associated with products including hydrophobic polymer film. This discomfort, for example, may be due to extended contact between fluid and the wearer's skin in normal use of products of this nature.

Accordingly, these products have had inherent and sometimes severe negative characteristics and less than favorable acceptance by some consumers.

In attempting to overcome the disadvantages of hydrophobic polymer film topsheets, devices have been designed to exhibit greater surface dryness. Hydrophobic polymer film topsheets have been created with openings or tapered capillaries for channeling fluid through the topsheet into the absorbent core in discrete points, so that the amount of fluid left on the wearer's skin is hopefully reduced. Tapered capillaries also have been designed to prevent "rewetting", which is reverse flow (reflow) of fluid from the absorptive core back through the topsheet and onto the skin. Rewetting can be caused by common bunching or compression of the product often encountered in normal use of absorptive devices. The tapered capillaries generally include excess material against the absorbent core that is designed to block the capillary in the reflow direction, however, are inefficient because each drop of liquid must contact a capillary in order for it to travel through the capillary into the absorbent core.

Consequently, there remains prolonged exposure of fluids to the wearer's skin. In addition, the amount, size and placement of the capillaries is critical for reducing the amount of fluid contacting the wearer as well as the wearer's length of exposure to the fluid. While location and structural characteristics of such capillaries can be optimally designed in theory, maintaining these critical parameters in use has been consistently unreliable in existing products.

In order to address these inefficiencies associated with hydrophobic polymer film topsheets, surfactants have sometimes been added to improve fluid flow through the topsheet. Surfactants modify the surface of an hydrophobic film topsheet to render it hydrophilic, i.e. to confer wettability, so that fluid more quickly passes through the topsheet to the absorbent core at discrete points. Wettability is the spreading of a fluid on a surface due to reduced surface tension of such flow and/or surface energy of the surface. However, the use of surfactant compromises the device's overall fluid handling ability when the surfactant is desorbed by bodily fluids. Fluids that pass through a topsheet having surfactant disposed thereon acquire some of the surfactant, which reduces the surface tension of the fluid and, in turn, compromises the effective absorbent properties of the absorbent core. Also, aging of the surfactant reduces its effectiveness at rendering the topsheet wettable, thereby reducing the effective "shelf-life" of any product including surfactant treatment. Surfactant also can be rubbed off the surface during handling and packaging. Another disadvantage to using surfactant is the increase in cost of production as well as possible allergic reactions and skin irritations.

Another attempt to overcome problems associated with the prior art devices is the use of hydrophilic material, usually in the form of a foamed sheet which is produced from hydrophilic groups and epoxy resins. However, a disadvantage associated with foamed sheets is their lack of utility as a formed film topsheet.

SUMMARY OF THE INVENTION

Accordingly, this invention provides an absorbent device having an improved topsheet which comprises a three-dimensional hydrophilic polymer film having a plurality of openings for more effectively removing fluid from a wearer's body. The openings being tapered capillaries each having a base in a surface plane of the topsheet and an apex remote from said surface plane. The angle of taper of the capillaries being from about 10° to about 60° from vertical and the base having an opening dimension from about 0.006 inches (0.152 mm) to about 0.250 inches (6.35 mm), and the apex having an opening dimension from about 0.004 inches (0.102 mm) to about 0.100 inches (2.54 mm). In addition, an opacifying agent, preferably about 2% by weight of titanium dioxide, is added to the nylon and polyetheramide to provide a clean, dry, and white appearance to the device. The length of contact of bodily fluids with the wearer is minimized due to the hydrophilic properties of this topsheet, as fluid spreads rapidly over the topsheet surface as well as onto the underside of the topsheet such that fluid is effectively dispersed to a larger area of the absorbent core. Thus, the need for surfactant to assist in initial fluid intake is eliminated while uniformity and reliability of absorbency of the entire device is further improved by eliminating the surfactant.

The topsheet of this invention thereby maintains the benefits of current art topsheets, such as a clean, dry, white appearance, and features outstanding rewetting properties. This topsheet additionally provides significant absorbent benefits over existing topsheets. The augmented absorbent benefits arise from the inherent and permanent hydrophilicity in the hydrophilic topsheet, and the elimination of the need for surfactant. The present topsheet immediately spreads fluid over the surface for absorption of bodily fluids away from the body into the absorbent core of the device while inhibiting reverse flow of these fluids; thus, a relatively drier and more comfortable surface is provided for contact with the user than previously obtainable. This device provides quicker and more complete absorption of bodily fluids so that hot, wet, sweaty and sticky feelings are minimized.

Accordingly, it is an object of this invention to overcome the deficiencies and inefficiencies of absorbent devices heretofore available in the industry.

It is also an object of this invention to provide a topsheet for absorptive devices comprising an hydrophilic film which permits improved absorption of bodily fluids from the body into the absorbent core, while effectively inhibiting the reverse flow of fluids from the absorbent core.

It is another object of this invention to provide an absorbent article which presents a drier and more comfortable topsheet surface to the wearer than has been previously obtainable.

It is a further object of this invention to provide a topsheet for absorptive devices having a plurality of tapered capillaries each having a base in a surface plane of the topsheet and an apex remote from the surface plane for draining fluid from the topsheet surface to the absorbent core.

It is yet another object of the invention to provide a topsheet for absorptive devices being constructed of nylon, polyetheramide, and an opacifying agent such as titanium dioxide.

BRIEF DESCRIPTION OF THE DRAWINGS

While the specification concludes with claims particularly pointing out and distinctly claiming the present invention, it is believed the same will be better understood from the following description taken in conjunction with the accompanying drawings in which:

DETAILED DESCRIPTION OF THE PREFERRED EMBODIMENT

This discussion is primarily directed to using the present invention as a unique absorptive structure, as may be embodied in a disposable sanitary pad. While this is contemplated as being a preferred use of the topsheet of the present invention, it should be understood that it also has substantial utility in a wide variety of disposable absorptive devices, such as diapers (for children as well as incontinent garments for adults), bed pads, towels, bandages and the like. The detailed description of the absorptive structure and its use in a disposable sanitary pad will allow one skilled in the art to readily adapt this invention to other devices.

Figure 1:
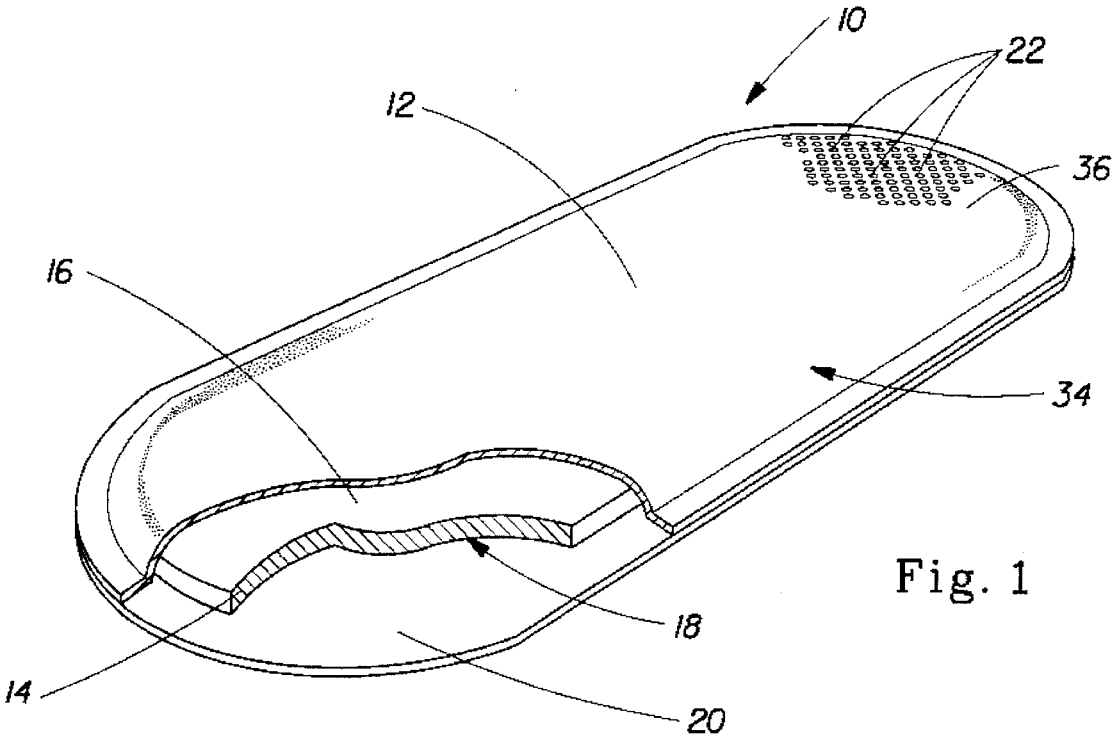
FIG. 1 is a perspective view of a sanitary pad employing the topsheet of this invention and having portions of its components cut away for clarity.

Referring now to the drawings in detail, wherein like numerals indicate the same elements throughout the views, FIG. 1 is a perspective view of a sanitary pad employing the topsheet of this invention where the device is referred to generally by reference numeral 10. The sanitary pad 10 comprises the topsheet 12 of this invention, an absorbent core 14, and a liquid impervious backsheet 20. The absorbent core 14 has two sides, the body facing side 16 which contacts the topsheet 12, and the garment facing side 18 which contacts the backsheet 20. Sanitary pad 10 may be made according to U.S. Pat. No. 4,950,264 issued to Osborn and incorporated herein by reference. Similarly, a diaper may be made according to U.S. Pat. No. 3,860,003 issued to Buell and incorporated herein by reference.

The topsheet 12 is preferably provided in the form of a three-dimensional hydrophilic polymer film of from about 0.0005 inches (0.0127 mm) to about 0.0020 inches (0.0508 mm) in thickness. There are many suitable resins from which those skilled in the art may make the topsheet of this invention, such as Nylon 6, or resins based on nylon chemistries; however, HYDROFIL®, a block copolymer of Nylon 6 and Polyetheramide, as commercially available from Allied Signal is particularly suitable. In addition, the formed film technology described in U.S. Pat. No. 4,342,314 to Radel et al. and U.S. Pat. No. 4,463,045 to Ahr et al. may be used with this topsheet and are incorporated herein by reference.

The poly(ethylene oxide) diamine (PEOD) block is prepared by first treating polyethylene glycol with propylene oxide to generate a polyether with terminal secondary hydroxyls. These hydroxyls are then converted to amines, creating a polyethylene glycol with amine ends. This polymer is then added to caprolactam prior to polymerization of the nylon. The resulting film has been found to be most useful in the present invention when the amount of polyetheramide is about 0% to about 23% by weight. Thus, the amount of nylon 6 is about 77% to about 100% by weight.

Since the polymer film would normally be clear, an opacifying agent 36 is preferably added to give the topsheet 12, and the disposable garment, a clean, dry, white appearance. A preferred opacifying agent 36 is titanium dioxide ($TiO_2$), wherein at least 2% of the film by weight is $TiO_2$. The most preferred PEOD:Nylon 6 weight ratio in the polymer film is about 15:85.

Figure 2:
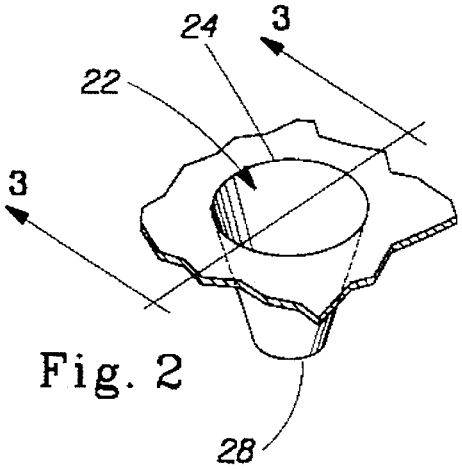
FIG. 2 is an enlarged fragmentary perspective view of a portion of the topsheet of FIG. 1 and a single tapered capillary.
Figure 3:
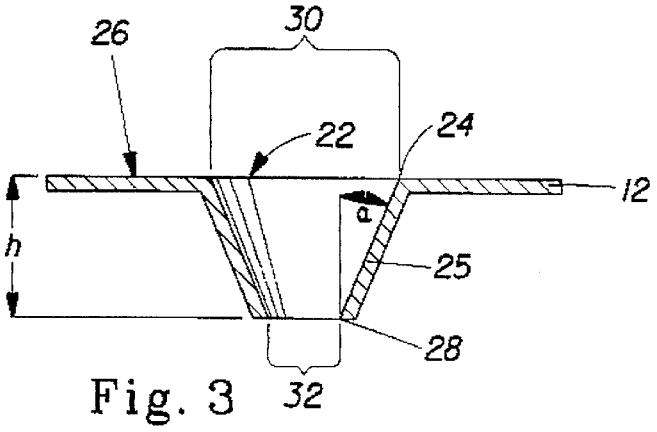
FIG. 3 is a partial, vertical cross-section of the tapered capillary of FIG. 2, taken along section line 3–3 thereof.

The three-dimensional topsheet 12 is preferably provided in the form of a formed film with a plurality of openings like that described by Radel et al. in U.S. Pat. No. 4,342,314, and incorporated herein by reference. The openings are preferably provided as tapered capillaries 22 and are shown in perspective in FIG. 2 and in cross-section in FIGS. 3 and 4. While tapered capillary 22 is shown as a frustrum of a conical surface shape (frusto-conical shape), it should be understood that any generally tapered structure, such as a frustrum of a pyramid or the like with a triangular, square, or polygonal base, is within the contemplation of the invention. Circular tapered capillaries are used in this exemplary description merely for convenience in explaining the manifold advantages of the invention.

Figure 4:
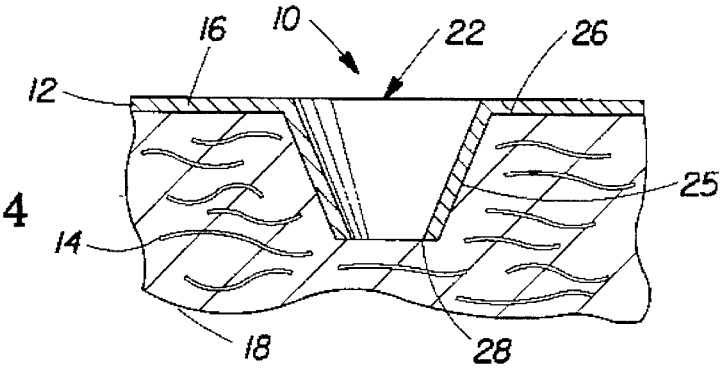
FIG. 4 is a partial, vertical cross-section of a tapered capillary as it would appear in a preferred sanitary pad as seen in FIG. 1, wherein the capillary is arranged in intimate contact with an absorbent core.

Various topsheet designs are possible, however, a preferred design is described below. The angle of taper of the sidewalls 25 of capillary 22 is represented by $\alpha$, and is preferably from about 10° to about 60° from vertical. Each tapered capillary 22 has a base 24 located adjacent a surface plane 26 of the topsheet 12, tapered sidewalls 25, and an apex 28 located remote from the surface plane 26 of the topsheet 12. Each tapered capillary 22 is of decreasing cross-section in the direction from base 24 to apex 28. Apex 28 is preferably maintained in intimate contact with an absorbent core 14 as best seen in FIG. 4. When the tapered capillary 22 is provided in a generally frusto-conical shape, the base opening dimension 30 and apex opening dimension 32 are chosen to allow fluid to readily pass from the surface 34 of the topsheet 12 to the absorbent core 14. Apex opening dimension 32 is preferably from about 0.004 inches (0.102 mm) to about 0.100 inches (2.54 mm), and preferably, from about 0.005 inches (0.127 mm) to about 0.020 inches (0.508 mm) in this sanitary pad application. The height of the tapered capillary is defined as the outermost surface of the topsheet 12 (i.e. the surface in contact with the wearer) and the apex 28 of tapered capillary 22.

The tapered capillary base opening dimension 30 is selected to satisfy two important criteria. The first is the subjective feel of the surface 34 of the topsheet 12 which, in many applications, contacts the skin of the user. It has been found that the hydrophilic polymer film is most comfortable when base opening dimension 30 is within the range from about 0.006 inches (0.152 mm) to about 0.250 inches (6.35 mm). Preferably, the base opening dimension 30 is within the range from about 0.030 inches (0.762 mm) to about 0.060 inches (1.524 mm). The second criterion is that the capillary base opening dimension 30 be sufficiently small to allow a liquid droplet of predetermined size (depending on the nature of the fluid to be absorbed) to bridge across at least one capillary 22. This criterion is achieved by the above dimensions in the sanitary napkin example. The remotely located apex 28 of the tapered capillary 22 enables direct and intimate contact between the fluid and the absorbent core 14 so that fluid is absorbed into the core as illustrated in FIG. 4. The topsheet 12 preferably is glued to the core to maintain intimate contact between the capillaries 22 and the absorbent core 14. In addition, pressure exerted by the wearer also contributes to maintaining intimate contact between the capillaries 22 and the core 14. The topsheet 12 and the backsheet 20 are heat sealed together along the edges of the pad 10 which also contributes to keeping the capillaries 22 in contact with the core 14. These same criteria are expected to be generally applicable to the present invention. However, further optimization of topsheet structure may be possible by virtue of the unique hydrophilic properties of the hydrophilic polymer film.

Figure 5:
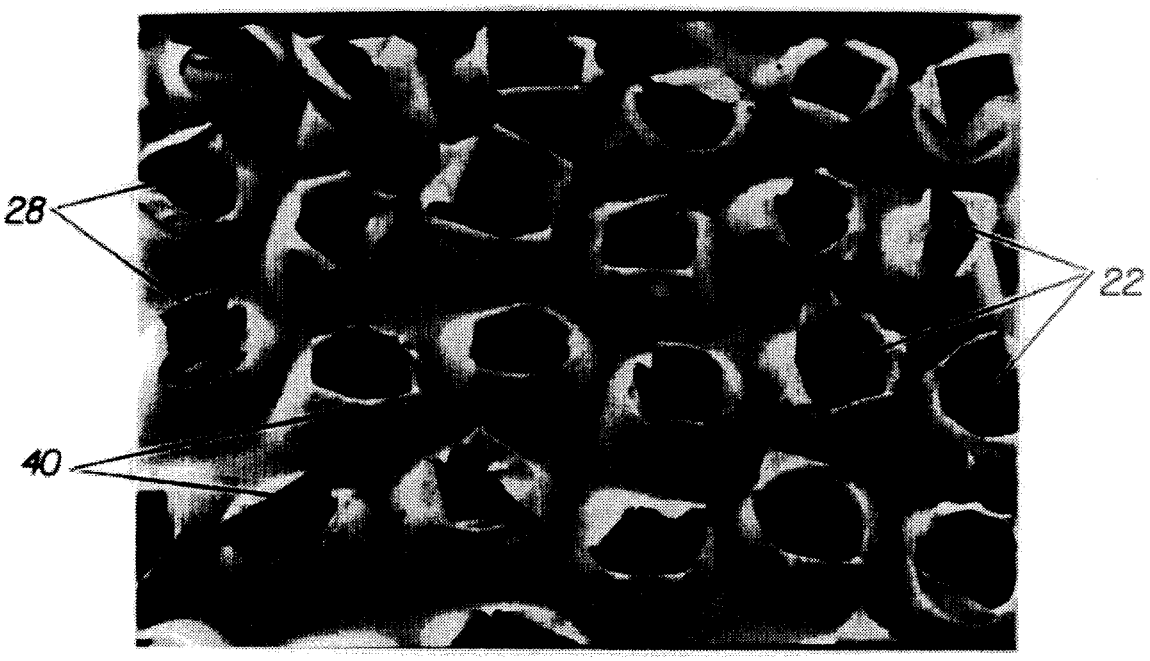
FIG. 5 is a bottom plan view photograph of the topsheet of the present invention at a 30° tilt from horizontal showing the apex flaps of the tapered capillaries in FIG. 1.

For maximum wearing comfort, absorptive devices must be constructed so there is no reverse flow of fluid when an absorbent article employing the absorptive device is placed under pressure as by the wearer sitting on or moving about after fluid has been absorbed in use. Protection from this pressure induced reverse flow is best obtained if the absorbent article is constructed so as to be less than totally saturated at its expected maximum fluid content. As shown in FIG. 5, apex flaps 40 adjacent each apex 28 are loose excess film material that remains after the capillaries 22 are formed. Apex flaps 40 provide protection against rewet or reflow by blocking the tapered capillaries when fluid flows in the reverse direction. The pressure of the fluid against the apex flaps essentially spreads the flap over the apex 28 opening such that reflow is prohibited. The tapered nature of capillaries 22, and the reduced size of apex opening dimension 32 also assist in minimizing the potential for such reverse flow which can lead to rewetting.

It is necessary for the topsheet 12 to allow rapid transfer of fluids into and through it. This rate of transfer depends on several variables, including rate of fluid discharge from the body, viscosity of the fluid, and proportion of open area of the topsheet and minimum opening dimensions of tapered capillaries.

Topsheet 12 provided with tapered capillaries 22 can be manufactured in any of several ways well known in the art, such as described in the Radel et al. and Ahr et al. patents. One particularly suitable method is to process the film with water jets to form the desired tapered capillaries 22.

In order to contribute to a better understanding of this invention and not by way of limitation, the following examples also are provided.

EXAMPLE I

The effect of the topsheet of the present invention on absorbent performance of a catamenial device as measured by standard strikethrough and rewet tests known in the industry was compared to several conventional topsheets. Samples for these tests were constructed by hand assembling the topsheet, core, and backsheet and securing the layers to each other with either double sided tape or glue. Strikethrough tests evaluate how quickly a device acquires fluid, whereas rewet tests evaluate the amount of fluid that passes from a device back to the skin of the wearer. Catamenial devices having no topsheet, a polyethylene formed film topsheet, a polyethylene formed film topsheet with surfactant, an HYDROFIL® formed film topsheet, a SONTARA® topsheet, and a HILOFT brand topsheet were tested. The device with no topsheet was used as a control device, where the top surface is represented by the airfelt core itself; polyethylene formed film was the topsheet used on the marketed ALWAYS® pad except with no surfactant; polyethylene formed film with surfactant was the topsheet used on the marketed ALWAYS® pad; and HYDROFIL® formed film refers to a topsheet of the present invention, SONTARA® is a known, commercially available nonwoven from rayon made by DuPont, and HILOFT brand material is a nonwoven material made by Scott paper and comprising a combination of 1.5 dpf, and 5.5 dpf hollow fibers at a total basis weight of 32.1 $g/m^2$.

Each topsheet was glued to the top of an absorbent core composed of common airfelt fluff (core basis weight at 530 $g/m^2$, and core density at 0.06 $g/cm^3$ at 0.13 psi (896.552 $N/m^2$)), and each had a polyethylene film backsheet to create a 3.75 inches (9.525 cm) by 3.75 inches (9.525 cm) catamenial device. Each device was then placed under a 4 inches (10.16 cm) by 4 inches (10.16 cm) strikethrough plate such that the topsheet was adjacent to the bottom of the plate. Three 5 ml increments of artificial menses fluid (preparation described in Weisman, U.S. Pat. No. 4,773,903 and incorporated herein by reference) were poured through an opening in the center of the strikethrough plate, and then one 10 ml increment was added. The strikethrough plate had electronic probes spanning the opening such that each time fluid passed through the opening, the probes were activated and started a timer. The probes and timer were deactivated when fluid no longer spanned the opening. The overall test sequence consisted of six steps (with a one minute interval between each step): 1 ) 5 ml of fluid poured through the opening into the device for a measurement of 5 ml strikethrough (S-T) time, 2) an additional 5 ml poured through the opening for a measurement of 10 ml S-T time), 3) Rewet value measured (10 ml fluid in the device), 4) an additional 5 ml poured through the opening for a measurement of 15 ml S-T time, 5) an additional 10 ml poured through the opening for a measurement of 25 ml S-T time, and 6) Rewet value measured (25 ml fluid in the device). The cumulative time for fluid to pass through the topsheet was recorded as a function of the total volume loaded in the pad and is shown in Table 1.

The rewet test was performed after the second 5 ml increment of fluid was poured and was repeated after the entire 25 ml of fluid was added. The rewet test was conducted by removing the strikethrough plate, placing tared filter paper on top of the device, and placing a 4 inches (10.16 cm) by 4 inches (10.16 cm) rewet weight on the surface of the device which generated a confining pressure of 0.25 psi (224.138 $N/m^2$). After 30 seconds, the rewet weight was removed and the amount of fluid that passed from the device into the filter paper was measured gravimetrically as the rewet value. The results are listed in Table 2. Confidence intervals for this test were calculated at the 95% confidence level, n=3.

TABLE 1

| | Cumulative Strikethrough Time (seconds) | | | |
|---|---|---|---|---|
| Topsheet | 5 ml | 10 ml | 15 ml | 25 ml |
| No Topsheet | 1.9 ± 0.3 | 6.0 ± 0.8 | 8.7 ± 3.2 | 17.0 ± 7.6 |
| Polyethylene Formed Film | 3.2 ± 0.9 | 9.4 ± 6.7 | 12.9 ± 8.2 | 27.9 ± 24.2 |
| Polyethylene Formed Film (with Surfactant) | 2.9 ± 0.1 | 7.0 ± 1.1 | 10.5 ± 2.4 | 23.4 ± 6.7 |
| HYDROFIL ® Formed Film | 2.6 ± 1.9 | 4.1 ± 2.8 | 5.7 ± 3.6 | 9.1 ± 5.1 |
| SONTARA ® | 2.2 ± 0.6 | 6.2 ± 1.4 | 10.5 ± 4.1 | 25.0 ± 10.1 |
| HILOFT | 3.5, n = 2 | 5.7, n = 2 | 8.2, n = 2 | 15.3, n = 2 |

TABLE 2

| | Rewet Value (grams) | |
|---|---|---|
| Topsheet | 10 ml | 25 ml |
| No Topsheet | 0.91 ± 0.21 | 2.37 ± 0.50 |
| Polyethylene Formed Film | 0.01 ± 0.01 | 0.04 ± 0.02 |
| Polyethylene Formed Film (with Surfactant) | 0.01 ± 0.01 | 0.05 ± 0.07 |
| HYDROFIL ® Formed Film | 0.01 ± 0.01 | 0.03 ± 0.00 |
| SONTARA ® | 0.87 ± 0.38 | 1.54 ± 0.49 |
| HILOFT | 0.17 ± 0.15 | 0.48 ± 0.60 |

The results indicate that devices having HYDROFIL® topsheets made in accordance with the present invention yield the best combination of fast rates of fluid acquisition (low strikethrough times), and best fluid containment under pressure (low rewet values). While not intended to limit the scope of the present invention, as presently understood, the fast acquisition rates were attributed to the hydrophilicity of the topsheet, which causes the fluid to spread quickly to the core, as well as the moisture sorption properties of the topsheet, which cause the topsheet to swell and buckle such that channels are formed that allow fluid to spread to a greater area of the core faster. Similarly, the favorable rewet results are attributed to the tapered capillary formed film structure which is maintained with the HYDROFIL® topsheet.

Similar results have been demonstrated using synthetic urine as the test fluid, reducing the increment of fluid addition to +2 ml (for a total of 10 ml added), and using a core having absorbent gelling material.

EXAMPLE 2

The topsheet of the present invention was evaluated for impact on absorbent performance of a catamenial device as measured through the fluid competition test. The fluid competition test evaluates how effectively a device partitions fluid away from a competing surface, such as human skin, to deliver absorbency and dryness perception.

In such testing, topsheets, as described above, were glued to the top of an absorbent core composed of airfelt fluff (core basis weight at 558 $g/m^2$) to which a polyethylene film backsheet was previously attached. The devices measured 3 inches (7.62 cm) by 3 inches (7.62 cm). The topsheet side of the device was placed in contact with 1.5 ml of artificial menses that was spread evenly over a 2.8 $in^2$ (18.066 $cm^2$) area of a flat cellophane surface which simulated a skin surface under a confining pressure of 0.18 psi (1241.379 $N/m^2$). After 30 seconds the device was removed, the cellophane surface was wiped clean with tared filter paper, and the amount of fluid left in contact with the cellophane was determined gravimetrically and is reported in Table 3 as the amount of residual fluid (in grams). Confidence intervals were calculated at the 95% confidence level, n=4.

The topsheet of the present invention was compared to several conventional topsheets for fluid competition test performance. In addition to the topsheets described in Example I, Hydrophilic Latex Coated Polyethylene Formed Film and Hydrophilic Atmer Treated Polyethylene Formed Film were tested. The Hydrophilic Latex Coated Polyethylene Formed Film was prepared as disclosed by Noda in U.S. Pat. No. 4,735,843 and incorporated in its entirety herein by reference. Hydrophilic Latex Coated Polyethylene Formed Film allows the surface of an hydrophobic sheet to be selectively rendered hydrophilic. Atmer antifog agent hydrophilizes the film's surface, but does not lower the fluid's surface tension if desorbed.

Results of the fluid competition test determinations for a topsheet of the present invention and several comparative topsheets are set forth in Table 3.

TABLE 3

| TOPSHEET | FLUID COMPETITION TEST (Residual Fluid, grams) |
|---|---|
| No Topsheet | 0.04 ± 0.01 |
| Polyethylene Formed Film | 0.16 ± 0.03 |
| Polyethylene Formed Film (With Surfactant) | 0.15 ± 0.03 |
| HYDROFIL ® Formed Film | 0.06 ± 0.03 |
| SONTARA ® | 0.03 ± 0.01 |
| Polyethylene Formed Film (With Hydrophilic Latex Coating) | 0.17 ± 0.03 |

The data indicate that devices covered with a formed film topsheet of the present invention yield fluid competition test results that are significantly better than other formed film topsheets, including topsheets with hydrophilized surfaces, and are comparable to the partitioning performance of nonwoven topsheets and to a device having no topsheet present. The strong partitioning capability of the HYDROFIL® formed film made in accordance with the present invention is believed to stem from the inherent hydrophilicity of the topsheet, as well as to its moisture sorption capability.

Having shown and described the preferred embodiments of the present invention, further adaptions of the topsheet shown and described herein can be accomplished by appropriate modifications by one of ordinary skill in the art without departing from the scope of the present invention. Several of these potential modifications have been mentioned, and others will be apparent to those skilled in the art. Accordingly, the scope of the present invention should be considered in terms of the following claims and is understood not to be limited to the details of structure and operation shown and described in the specification and drawings.

What is claimed is:

1. A topsheet for an absorbent article, said topsheet comprising a three-dimensional hydrophilic polymer film having a plurality of openings for fluid passage, said openings being tapered capillaries each having a base in a surface plane of said topsheet and an apex remote from said surface plane, said capillaries having an angle of taper such that said tapered capillaries are of decreasing cross-section in the direction from said capillary base to said capillary apex, said film having inherent and permanent hydrophilic properties whereby said film has hydrophilic properties without the necessity of a surface active agent.

2. The topsheet of claim 1 wherein said film is a copolymer of nylon 6 and polyetheramide.

3. The topsheet of claim 2 wherein the copolymer is up to 23% by weight polyetheramide.

4. The topsheet of claim 1 wherein said film further includes an opacifying agent for providing said topsheet with a clean, dry and white appearance.

5. The topsheet of claim 4 wherein said opacifying agent is titanium dioxide, wherein said titanium dioxide comprises at least 2% of said film by weight.

6. The topsheet of claim 1 wherein said tapered capillaries have an angle of taper from about 10° to about 60°, said base has an opening dimension from about 0.006 inches (0.152 mm) to about 0.250 inches (6.35 mm), and said apex has an opening dimension from about 0.004 inches (0.102 mm) to about 0.100 inches (2.54 mm).

7. The topsheet of claim 1 wherein said tapered capillaries are positioned substantially perpendicular to said topsheet surface plane.

8. An absorbent article, comprising a topsheet and an absorbent core, wherein said topsheet is a three dimensional hydrophilic polymer film having inherent and permanent hydrophilic properties and being devoid of any surface active agent, said film further having a plurality of openings comprising tapered capillaries each having a base in a surface plane of said topsheet and an apex remote from said surface plane, said capillaries having an angle of taper such that said tapered capillaries are of decreasing cross-section in the direction from said capillary base to said capillary apex.

9. The absorbent article of claim 8 wherein said film is a block copolymer of nylon 6 and polyetheramide.

10. The absorbent article of claim 9 wherein the polyetheramide component of said block copolymer is about 0% to about 23% by weight of said copolymer.

11. The absorbent article of claim 8 further includes a fluid-impervious backsheet.

12. The absorbent article of claim 11 wherein said article is a sanitary pad.

13. The absorbent article of claim 11 wherein said article is a diaper.

14. The absorbent article of claim 11 wherein said article is an incontinence pad.

15. The absorbent article of claim 8 wherein said tapered capillaries have an angle of taper from about 10° to about 60°, said base having an opening dimension from about 0.006 inches (0.152 mm) to about 0.250 inches (6.35 mm), and said apex having an opening dimension from about 0.004 inches (0.102 mm) to about 0.100 inches (2.54 mm).

16. The absorbent article of claim 8 wherein said tapered capillaries are positioned substantially perpendicular to said topsheet surface plane.

17. An absorbent article, comprising:

an absorbent core having a body facing side and a garment facing side;

a fluid-impervious backsheet overlaying at least a portion of said garment facing side of said core; and a three-dimensional hydrophilic polymer film topsheet having inherent and permanent hydrophilic properties and a surface plane, said topsheet overlaying at least a portion of said body facing side of said core, said topsheet having a plurality of openings for fluid passage, said topsheet being formed of a copolymer of nylon 6 and polyetheramide, the copolymer being about 15% polyetheramide by weight;

said openings comprising tapered capillaries in the form of a frustrum of a cone, each having a base in a surface plane of said topsheet, and an apex remote from said surface plane, said capillaries having an angle of taper such that said tapered capillaries are of decreasing cross-section in the direction from said capillary base to said capillary apex, said angle of taper ranging from about 10° to about 60°, said base having an opening dimension from about 0.006 inches (0.152 mm) to about 0.250 inches (6.35 mm), and said apex having an opening dimension from about 0.004 inches (0.102 mm) to about 0.100 inches (2.54 mm); and wherein said absorbent core is located adjacent the apexes of said capillaries in use.

18. The absorbent article of claim 17 wherein said absorbent article is a sanitary pad.

19. The absorbent article of claim 16 wherein said absorbent article is a diaper.

20. The absorbent article of claim 16 wherein said article is an incontinence pad.

* * * * *